US009067013B2

(12) United States Patent
Wright et al.

(10) Patent No.: US 9,067,013 B2
(45) Date of Patent: Jun. 30, 2015

(54) MEDICAL ARTICLE SECUREMENT DEVICE

(75) Inventors: Clifford A. Wright, San Diego, CA (US); Adam S. Henry, Oceanside, CA (US); Robert F. Eisele, Carlsbad, CA (US); Thomas Jackson, La Jolla, CA (US); Tom Lorenzana, Spring Valley, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 581 days.

(21) Appl. No.: 12/601,352

(22) PCT Filed: Oct. 24, 2008

(86) PCT No.: PCT/US2008/081216
§ 371 (c)(1),
(2), (4) Date: Nov. 23, 2009

(87) PCT Pub. No.: WO2009/055739
PCT Pub. Date: Apr. 30, 2009

(65) Prior Publication Data
US 2010/0179483 A1    Jul. 15, 2010

Related U.S. Application Data

(60) Provisional application No. 60/982,334, filed on Oct. 24, 2007.

(51) Int. Cl.
*A61M 5/32* (2006.01)
*A61M 5/158* (2006.01)
*A61M 25/02* (2006.01)

(52) U.S. Cl.
CPC .............. *A61M 5/158* (2013.01); *A61M 25/02* (2013.01); *A61M 2025/024* (2013.01); *A61M 2025/028* (2013.01)

(58) Field of Classification Search
CPC ................ A61M 25/02; A61M 25/01; A61M 2025/0206; A61M 2025/024; A61M 2025/0246
USPC ............ 604/174, 177, 178, 180, 165.03, 158, 604/264; 24/3.1, 338, 327
See application file for complete search history.

(56) References Cited

U.S. PATENT DOCUMENTS 5,069,206 A    12/1991  Crosbie
5,267,967 A  * 12/1993  Schneider ..................... 604/174
(Continued)

FOREIGN PATENT DOCUMENTS

WO        WO 00/48658       8/2000
WO        WO 2004/016309    2/2004
(Continued)

*Primary Examiner* — Emily Schmidt
*Assistant Examiner* — Bradley G Thomas, Jr.
(74) *Attorney, Agent, or Firm* — Rutan & Tucker, LLP (57) ABSTRACT

A securement device (10) secures a medical article (12) to the body of a patient and prevents longitudinal movement of the medical article (12) relative to the securement device (10). The securement device (10) includes a base portion (50) that is disposed over at least a part of a securement piece (20). The securement piece (20) forms a channel (19) configured to receive at least a portion of the medical article (12). The device (10) includes at least one actuator (40). The at least one actuator (40) is coupled with the securement piece (20) and configured to move the securement piece (20) between open position and a closed position. When the securement piece (20) is in the open position, it can receive at least a portion of the medical article (12). When the securement piece (20) is in the closed position, it prevents the received medical article (12) from moving in the longitudinal direction relative to the securement device (10). In some embodiments the securement piece (20) has engagement members (23) extending from the inner surface of the securement piece (20). In an embodiment, the securement device (10) includes an opening (28) that receives an outwardly extending member of the medical article (12).

17 Claims, 13 Drawing Sheets

(56) References Cited

U.S. PATENT DOCUMENTS

| | | | |
|---|---|---|---|
| 5,312,375 A * | 5/1994 | Gurmarnik | 604/264 |
| 5,382,239 A * | 1/1995 | Orr et al. | 604/177 |
| 5,470,321 A * | 11/1995 | Forster et al. | 604/174 |
| 5,916,200 A | 6/1999 | Eppley et al. | |
| 6,245,044 B1 * | 6/2001 | Daw et al. | 604/158 |
| 6,523,231 B1 * | 2/2003 | Lassiter | 24/339 |
| 6,972,003 B2 * | 12/2005 | Bierman et al. | 604/180 |
| 7,014,627 B2 * | 3/2006 | Bierman | 604/174 |
| 7,377,472 B2 | 5/2008 | Brown et al. | |
| 7,776,017 B2 | 8/2010 | Ponzi et al. | |
| 8,251,956 B2 | 8/2012 | Bierman et al. | |
| 2004/0204685 A1 | 10/2004 | Wright et al. | |
| 2006/0247577 A1 | 11/2006 | Wright | |
| 2009/0143740 A1 | 6/2009 | Bierman et al. | |

FOREIGN PATENT DOCUMENTS

| | | |
|---|---|---|
| WO | WO 2004/022140 | 3/2004 |
| WO | WO 2011/133818 | 10/2011 |

* cited by examiner

MEDICAL ARTICLE SECUREMENT DEVICE

CROSS-REFERENCE TO RELATED APPLICATIONS

This application is the National Stage of International Application No. PCT/US2008/081216, filed on Oct. 24, 2008, entitled medical article MEDICAL ARTICLE SECUREMENT DEVICE, which claims the benefit of U.S. Provisional Patent Application No. 60/982,334, filed Oct. 24, 2007, both of which are hereby expressly incorporated by reference in their entireties.

BACKGROUND OF THE INVENTION

1. Field of the Invention

This invention relates to a securement device used to secure a medical article or medical article fitting to a patient.

2. Description of the Related Art

It is often necessary to introduce fluids and liquid medications directly into a blood vessel of a patient. Various types of medical articles, such as catheters, are often used in combination with connectors and syringes. A catheter is essentially a tube inserted through an incision in the skin into a blood vessel in the patient's body, generally without surgery. A simple intravenous (IV) line is usually acceptable for introduction of fluids and liquid medications into a blood vessel for short term general use. IV lines are typically inserted into a patient's arm by inserting a catheter or some other medical article, containing a needle, which pierces the skin, into a blood vessel. The needle is removed and discarded, while the medical article remains in the blood vessel.

It is important to minimize movement of the inserted medical article. If the medical article is not properly secured in place, it may be inadvertently displaced from its intended location. Consequently, medication delivered through the IV line may be released at an incorrect position. Furthermore, repeated back and forth movement of the medical article, or pistoning, can cause irritation of the blood vessel, disrupt proper introduction of medications to the patient, and increase the potential for bleeding or infection at the medical article insertion site. If extensive movement occurs, the IV line could even come out of the patient, interrupting delivery of medication and requiring re-insertion, often with hospitalization.

In the past, medical articles, such as catheters, were typically taped into place on the patient's skin. However, taping is time consuming and labor intensive. Tape also collects bacteria and must be frequently removed and replaced. More importantly, taping is not necessarily effective for securing a medical article in place on a patient. Sutures have also been used to attach medical articles to patients. With sutures, the medical article is stitched onto the skin. Sutures, however, can also be a source of infection, can cause pain and inflammation, and can make it more difficult to clean around the insertion site. Sutures also require time and skill to apply, and can cause scarring.

More recently, manufactured medical article anchors or securing devices have become widely adopted. While various designs have been developed, these devices are typically relatively inefficient or difficult to operate or manipulate. Thus, engineering design challenges remain to providing reliable, secure, and efficient medical article anchoring devices. Accordingly, improved medical article anchoring devices are needed.

SUMMARY OF THE INVENTION

One aspect of the present invention thus involves a retainer for a medical article. The retainer comprises a body member forming a channel configured to receive at least a portion of a medical article, the channel having a longitudinal axis. The body member moves between an open position and a closed position, the portion of the medical article being secured in the channel at least when the body member is in the closed position. The retainer further comprises at least one or more actuators coupled to the body member and configured to move the body member to the open position so as to receive the portion of the medical article in the channel. The retainer further comprises a base portion disposed over at least a portion of the body member, the base portion having one or more passageways configured to receive at least a portion of the one or more actuators.

Another aspect is a retainer for a medical article. The retainer comprises a body member that forms a channel configured to receive at least a portion of a medical article, the channel having a longitudinal axis. The retainer further comprises a latch member configured to move between a lock position and an unlock position. The latch member compresses the body member towards the longitudinal axis so as to secure the received portion of the medical article when in the lock position.

Another aspect of the present invention involves a retainer for a medical article. The retainer comprises a body member forming a channel configured to receive at least a portion of a medical article, the channel having a longitudinal axis. The body member is made of a first material and moves between an open position and a closed position, the portion of the medical article being secured in the channel at least when the body member is in the closed position. The retainer further comprises a base portion disposed over at least a portion of the body member, the base portion being made of a second material. The retainer also comprises at least one or more actuators coupled to the body member and being configured to move the body member to the open position so as to receive the portion of the medical article in the channel, at least a portion of the at least one or more actuators being made from a third material, the third material being different from at least one of the first material and second material. The retainer further comprises a pad supporting the base portion and having a lower surface, at least a portion of the lower surface being covered by an adhesive.

Further aspects, features and advantages of the present invention will become apparent from the detailed description of the preferred embodiments that follows.

BRIEF DESCRIPTION OF THE DRAWINGS

In the drawings, the same element number indicates the same element in each of the views.

DETAILED DESCRIPTION OF THE PREFERRED EMBODIMENTS

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

To assist in the description of these components of the securement device, the following coordinate terms are used. A "longitudinal axis" is generally parallel to a portion of the medical article retained by the securement device, as well as parallel to the axis of a channel of the securement piece, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal" are used consistently with the description of the exemplary application. Thus, proximal and distal are used in reference to the center of the patient's body.

Turning now to the drawings, in a first embodiment, as shown in FIGS. 1-5, a securement device 10 is configured to receive, secure, or stabilize a medical article or medical article fitting 12, for example, an IV (intravenous) catheter, peripheral IV catheter, IV hub, IV luer, IV adaptor or extension, or any other suitable medical article or fitting. A "medical article fitting" as used herein includes any type of medical article fitting, attachment, accessory, hub, connector, and so forth, whether integral with the medical article or as a separate piece from the medical article. Furthermore, the term "medical article" as used herein may refer to a medical article alone, a medical article fitting alone, or a medical article in combination with any type of medical article fitting.

Figure 2:
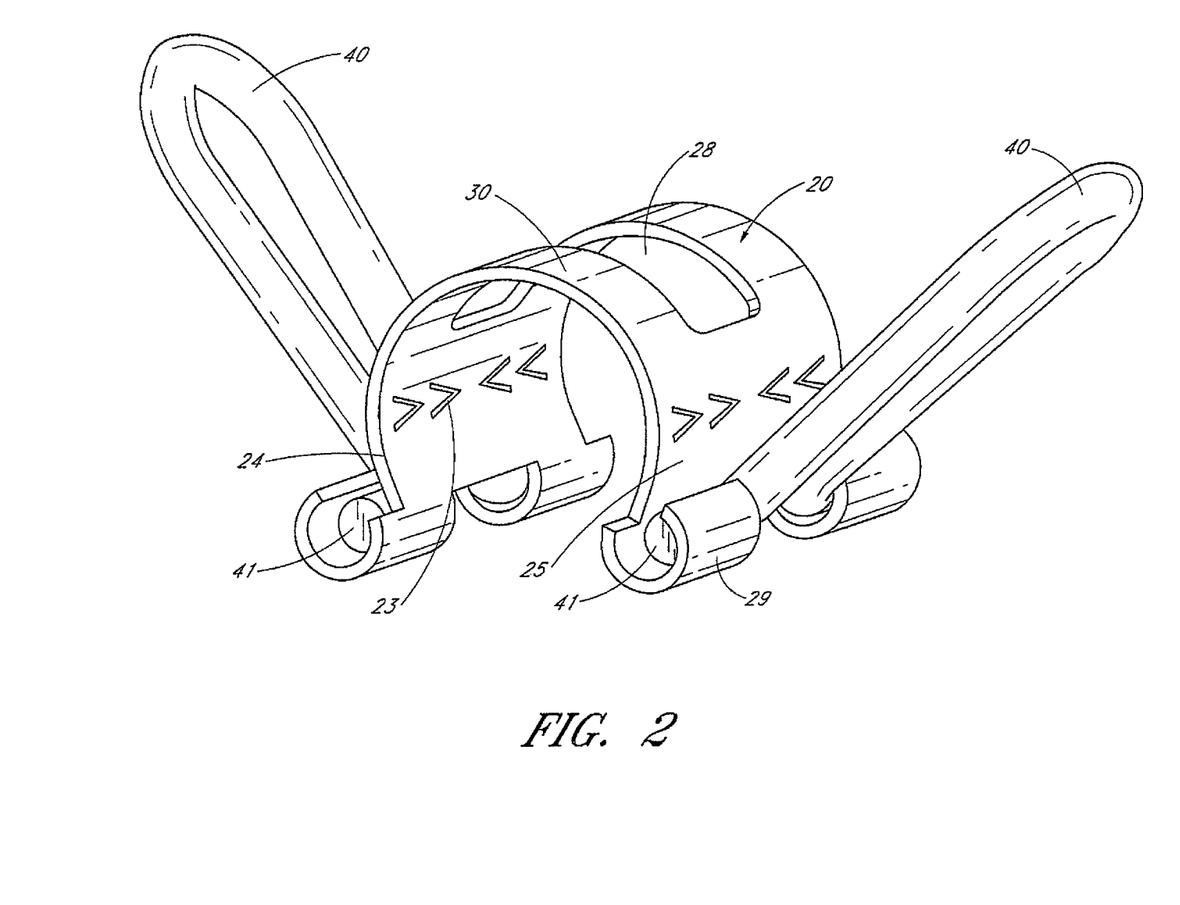
FIG. 2 is a perspective view of the securement piece of the securement device shown in FIG. 1.

As shown in FIG. 2, the securement device 10 includes a substantially longitudinal securement piece 20 having a central opening 19 for receiving a medical article 12. The securement piece 20 may be substantially arch-shaped, semi-cylindrical, or generally contoured to fit over or around a medical article 12. An upper region of the securement piece 20 preferably slopes generally in the longitudinal direction at an angle suitable to facilitate insertion of a needle, catheter, or other medical article into a patient. In one embodiment, the angle may be about 4-10°, or 5-9°, or 6-8°. Accordingly, a medical article 12 may be positioned within the sloped or angled securement piece 20 and directed toward the patient at an angle allowing for optimum flow, delivery, or drainage of any fluid to or from the patient.

One or more engagement members 23 or other protrusions extend from the inner surface of one or both side walls 24, 25 of the securement piece 20. The engagement members 23 may extend from the inner surface at an angle of 0-90° relative to the side walls 24, 25. Preferably, the engagement members 23 extend from the inner surface of the side walls 24, 25 at an angle of 25-65°, or 35-55°, or approximately 45°.

In the illustrated embodiment, a row of engagement members 23 is positioned on the inner surface of each side wall 24, 25 of the securement piece 20. The engagement members 23 are arranged in two pairs on each side wall 24, 25, with the pairs extending in opposite directions, toward each other, at approximately 45° angles. Alternatively, every engagement member 23 may extend in the same direction as one another, or each engagement member may be oriented in a direction opposite its neighboring engagement members 23.

Positioned generally toward the center of the top portion 30 of the securement piece 20 is a clearance opening 28. The clearance opening 28 is of a size sufficient to receive a tab or other extension from a medical article 12. In one embodiment, the clearance opening 28 is of a size sufficient to allow the tab or extension to pass or extend through the clearance opening 28 without contacting the sides or perimeter bordering the clearance opening 28.

Extending from the bottom of the side walls 24, 25 of the securement piece 20 are one or more arm receptacles 29. In the illustrated embodiment, a pair of arm receptacles 29 extend from each side wall 24, 25. The arm receptacles 29 may be substantially semi-cylindrical or have any other configuration suitable for receiving ends of an actuator arm 40 or other member used to expand or "open" the securement piece 20. In one embodiment, two spaced apart arm receptacles 29 extend from the bottom of each side wall 24, 25.

Two arms 40 are shown in the illustrated embodiment. The arms 40 are generally U-shaped and include substantially perpendicularly extending (relative to a centerline of the U-portion of the arm 40) end portions 41. The arms 40 may alternatively be rectangular, circular, oval, or have any other shape or configuration suitable for attachment to the securement piece 20, and for manipulation by a user to expand the securement piece 20.

As shown in FIG. 2, the end portions 41 of the arms 40 are securely positioned in the arm receptacles 29. For example, the end portions 41 may be snapped or otherwise inserted into the arm receptacles 29 such that they are securely held therein, yet are permitted to freely rotate or pivot within the arm receptacles 29. The arms 40 are preferably constructed of a hard, rigid material such as, for example, metal or plastic. The arms 40 may optionally be covered with a soft material 42, for example, rubber, foam, or latex, to provide an aesthetically pleasing appearance and a comfortable gripping surface. The aim covering 42 also provides increased surface area to facilitate expanding or opening of the securement piece 20 via inward force applied to the arms 40. The soft covering may optionally include ridges or ribs to increase traction and facilitate gripping and operation of the arms 40.

Figure 3:
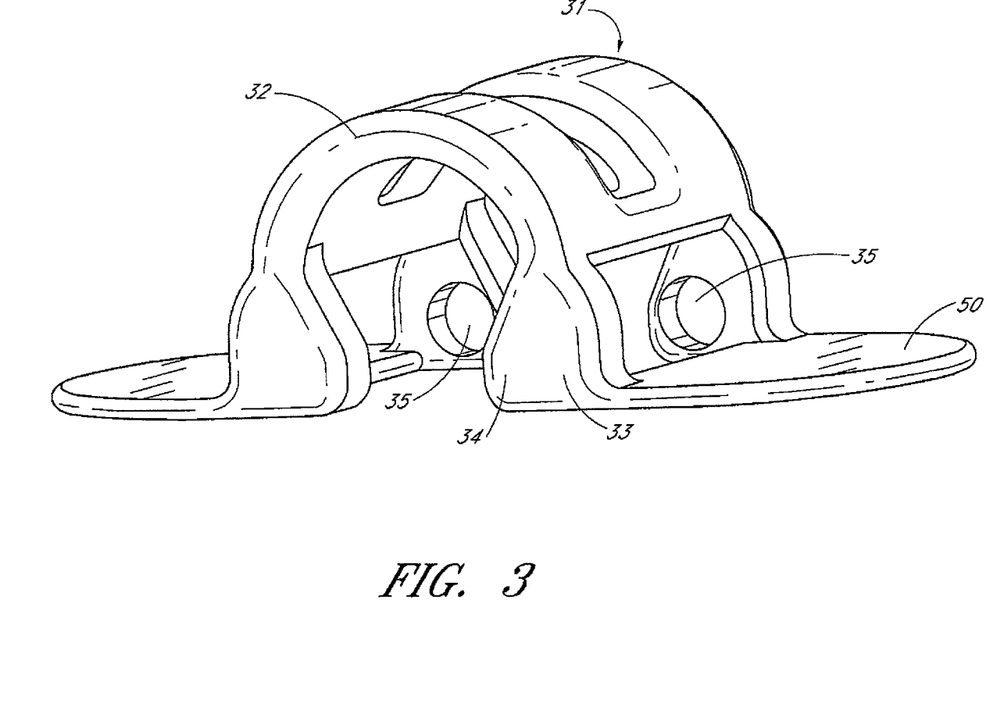
FIG. 3 is a perspective view of the shell of the securement device shown in FIG. 1.

A shell 31 optionally covers or encases the securement piece 20. The shell 31 is preferably made of a soft material, for example, rubber, foam, or latex, to provide a more aesthetically pleasing appearance and increased comfort for a patient. As shown in FIG. 3, the shell 31 includes a top portion 32, which generally corresponds to and fits around the top portion 30 of the securement piece 20. Extending downwardly from each corner of the top portion 32 is a shell wall 33. One or more of the shell walls 33 optionally includes an inner portion 34 protruding inwardly toward the longitudinal axis of the securement piece 20. The inner portions 34 may aid in preventing longitudinal movement of a medical article 12 through the securement piece 20. Each shell wall 33 includes an opening 35 on its inner surface for receiving an arm receptacle 29 of the securement piece 20. The opening 35 may have varying depths suitable for receiving arm receptacles 29 of varying sizes, or the opening 35 may be a hole that extends entirely through the wall 33.

In the illustrated embodiment, two base portions 50 extend laterally from the shell walls 33. The base portions 50 may be rigid, or may be generally flexible or contoured to conform to a specific patient site. A hydro-colloidal pad or other cushion may optionally be attached to an underside of each of the base portions 50 for providing increased patient comfort. The specific pad shape and size may vary. The underside of each of the base portions 50 (or of the cushions, if present) preferably includes an adhesive layer covered by a peelable strip 52. The peelable strips 52 are removable such that the adhesive may be exposed and the base portions 50 may be adhered to a desired securement site.

Each base portion 50 preferably includes a separate peelable strip 52 such that the central opening 19 of the securement device 10 is not blocked by a peelable strip 52. This allows the securement device 10 to be placed over the top of a medical article 12 before removing the strips 52 and adhering the device 10 to the patient. Alternatively, a single peelable strip may extend over the underside of both base portions 50. In such an embodiment, the strip 52 is removed prior to attaching the securement device 10 to a medical article 12. Alternatively, the securement device 10 may be affixed to a patient by applying adhesive tape over or around the device 10 or the base portions 50 and against the patient site.

Figure 1:
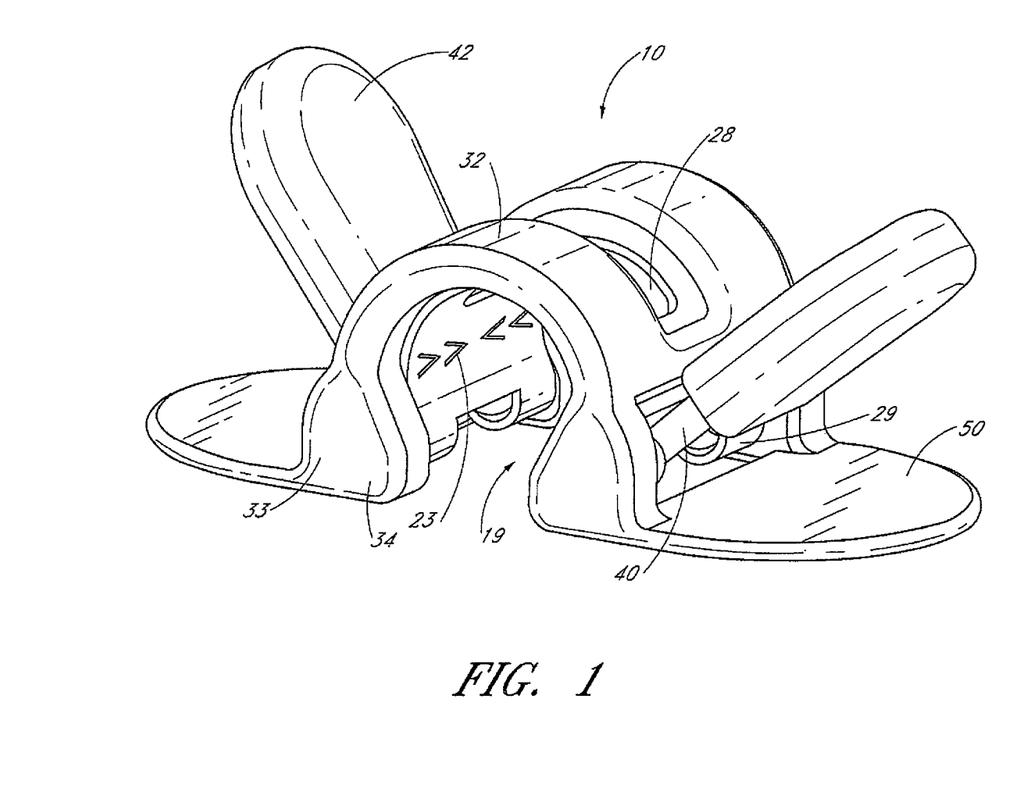
FIG. 1 is a perspective view of a securement device, according to one embodiment.
Figure 4:
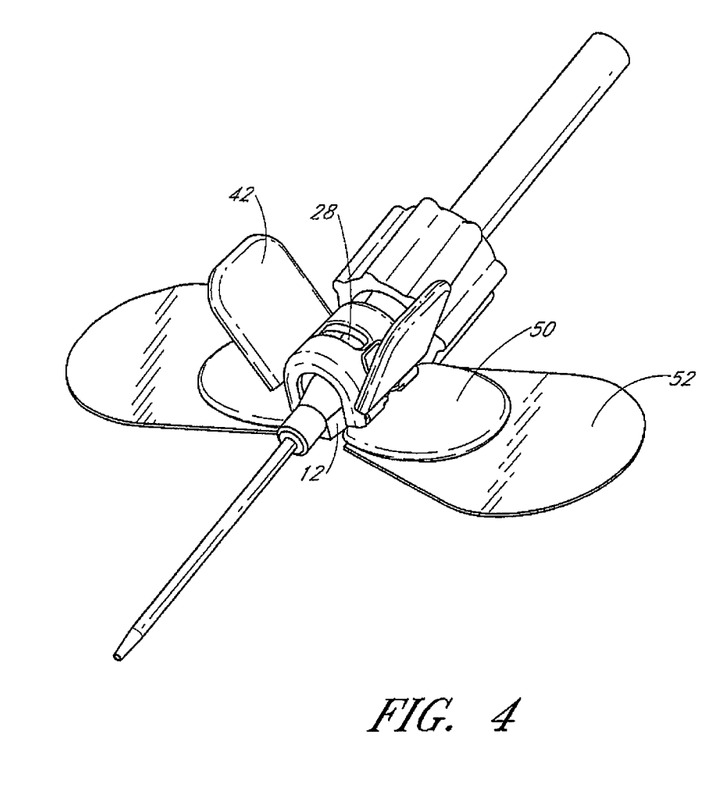
FIG. 4 is a perspective view of the securement device shown in FIG. 1 engaging a catheter fitting.
Figure 5:
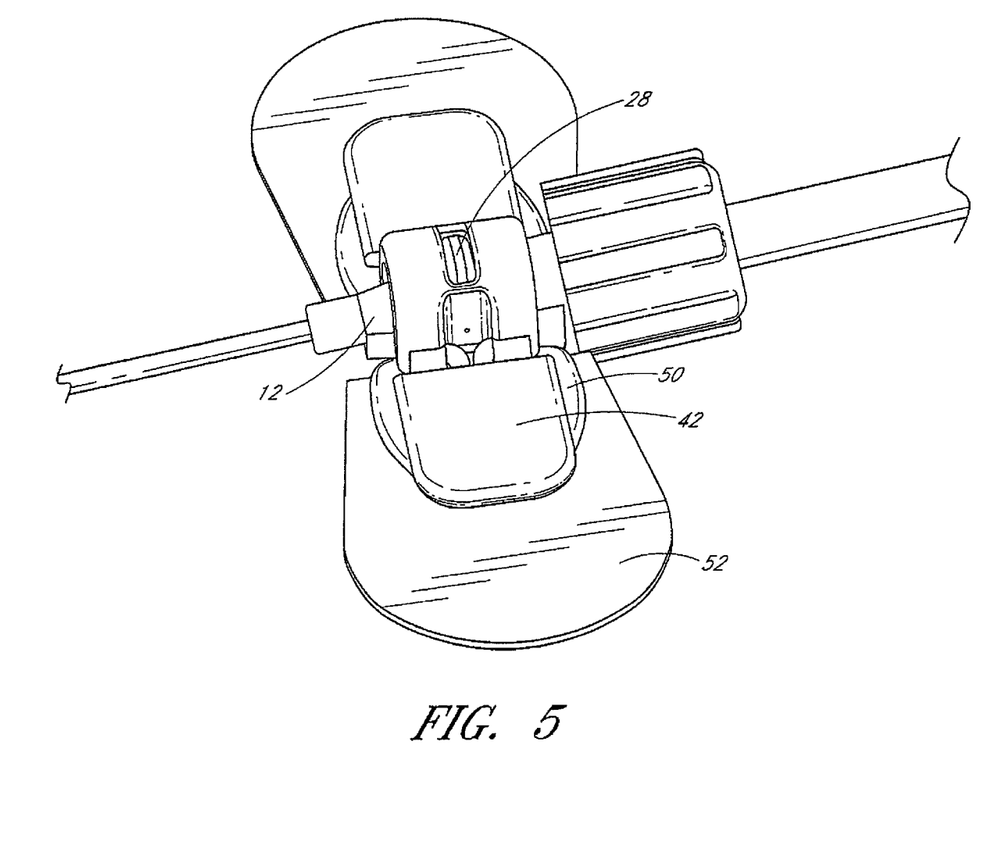
FIG. 5 is a perspective view of the securement device shown in FIG. 4 with the arms in a lowered position.

In use, the arms 40 are raised into the "up" position, as shown in FIGS. 1 and 2. An attendant squeezes the arms 40 toward each other, causing the central opening 19 in the securement piece 20 to widen so the securement device 10 may be placed over a medical article 12. The attendant then releases the arms 40, allowing the securement piece 20 to close or tightly conform around the medical article 12, as shown in FIG. 4. In this position, the engagement members 23 (possibly in conjunction with the inner portions 34 of the shell walls 33, depending on the configuration of the medical article 12) secure the medical article 12 in place and substantially prevent it from moving longitudinally within the securement device 10. The attendant may then lower the arms 40, into the position shown in FIG. 5, so they are not obtrusive. Finally, the attendant may remove the peelable strips 52, exposing the adhesive, and press the base portions 50 against a patient to adhere the securement device 10 containing the medical article 12 to the patient's skin.

Turning to FIGS. 6-9, in an alternative embodiment, a securement device 60 includes a substantially longitudinal securement body 62 including a central opening 64 for receiving a medical article 66. The securement body 62 may be substantially arch-shaped, semi-cylindrical, or generally contoured to fit over or around a medical article. An upper region of the securement body 62 preferably slopes generally in the longitudinal direction at an angle suitable to facilitate insertion of a needle or other medical article into a patient. In one embodiment, the angle may be about 4-10°, or 5-9°, or 6-8°. Accordingly, a medical article may be positioned within the sloped or angled securement body 62 and be directed toward the patient at an angle allowing for optimum flow, delivery, or drainage of any fluid to or from the patient.

Figure 6:
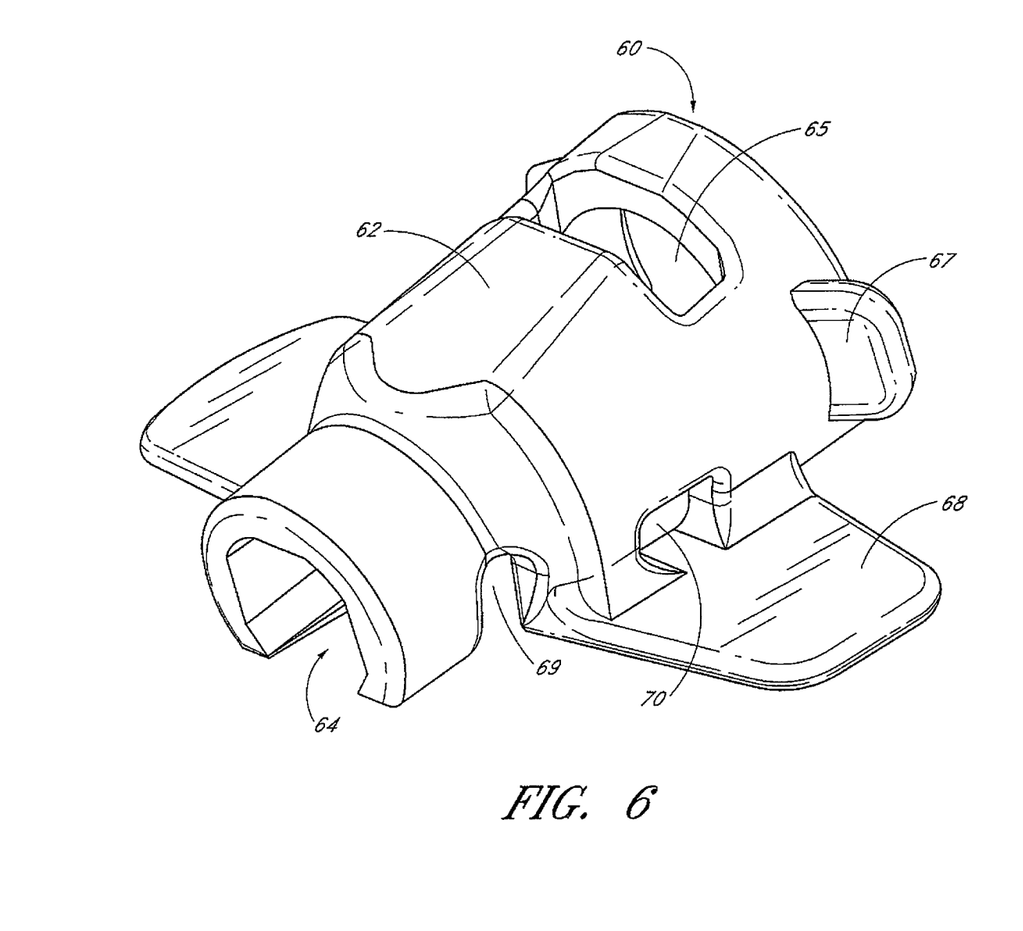
FIG. 6 is a front-right perspective view of a securement device, according to another embodiment.
Figure 7:
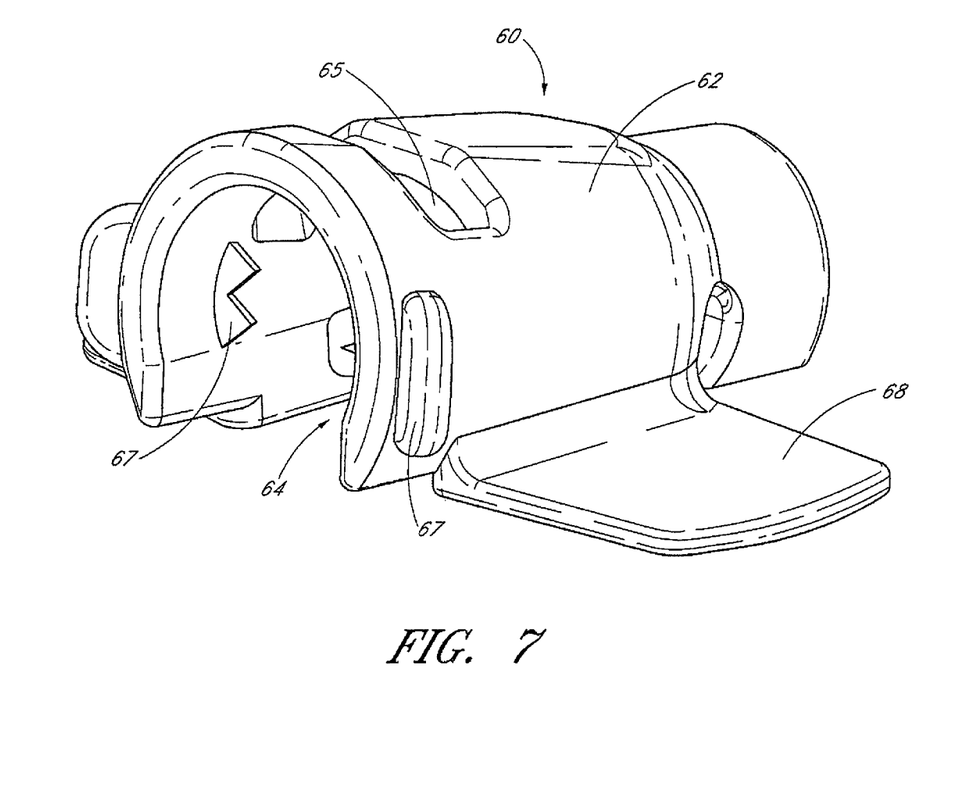
FIG. 7 is a rear-right perspective view of the securement device shown in FIG. 6.
Figure 8:
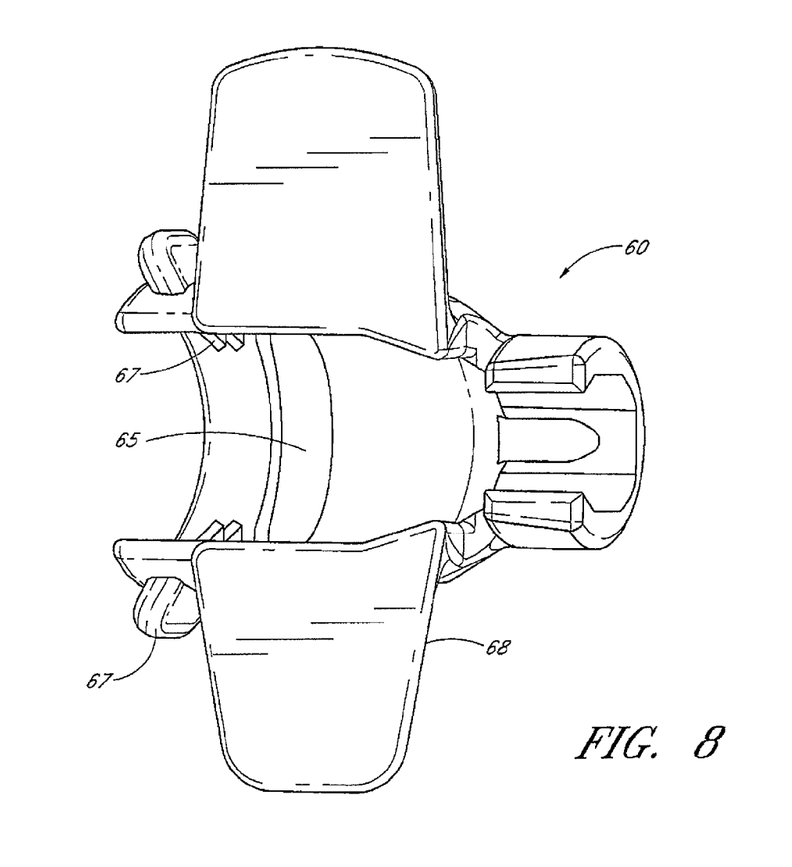
FIG. 8 is a bottom perspective view of the securement device shown in FIGS. 6-7.

The upper portion of the securement body 62 preferably includes a clearance opening 65. The clearance opening 65 is of a size sufficient to receive a tab or other extension from a medical article 12. In one embodiment, the clearance opening 65 is of a size sufficient to allow a tab or extension to pass or extend through the clearance opening 65 without contacting the sides or perimeter bordering the clearance opening 65. The securement body 62 optionally includes one or more notches 69 for accommodating one or more laterally extending members of a medical article. In one embodiment, a latch receptacle 70 or similar opening may be included in a side wall of the securement body 62 for receiving a latch of an optional cover, as described below.

One or more engagement members 67 or other protrusions preferably extend into the interior of the securement body 62. The engagement members 67 may extend at an angle of 0-90° relative to the interior walls of the securement body 62. Preferably, the engagement members 67 extend at an angle of 25-65°, or 35-55°, or approximately 45° relative to the interior walls. In the illustrated embodiment, two opposing engagement members 67 are positioned near the rear of, and extend into the interior of the securement body 62 at angles of approximately 45° relative to the side walls of the securement body 62. Any other suitable number of engagement members 67 may alternatively be included on the securement body 62.

The securement body 62 further includes one or more base portions 68 extending laterally from lower side regions of the securement body 62. The base portions 68 may be rigid, or may be generally flexible or contoured to conform to a specific patient site. A hydro-colloidal pad or other cushion may optionally be attached to an underside of each of the base portions 68 to provide increased patient comfort. The specific pad shape and size may vary. The underside of each of the base portions 68 (or of the cushions, if present) preferably includes an adhesive layer, which may be covered by one or more peelable strips (not shown), as described in the first embodiment. The one or more peelable strips are removable such that the adhesive may be exposed and the base portions 68 may be adhered to a desired securement site.

Figure 9:
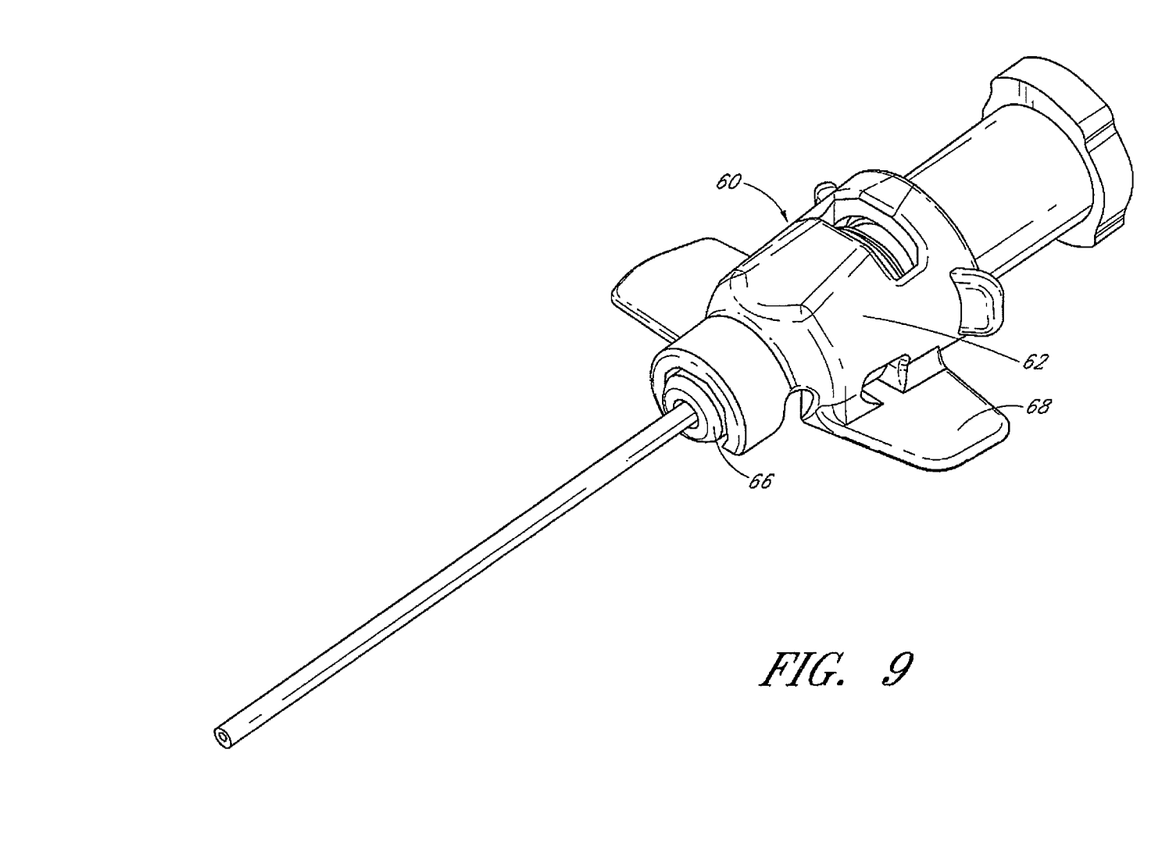
FIG. 9 is a perspective view of the securement device shown in FIGS. 6-8 engaging a catheter fitting.

In use, an attendant may pull the base portions 68 laterally away from each other to widen the central opening 64 so that it may be placed over a medical article 66. The attendant may then release the base portions 68 so that the securement body 62 closes or securely conforms around the medical article 66, as shown in FIG. 9. Alternatively, the attendant may snap the securement body 62 over top of the medical article 66. The attendant may then remove the peelable strips, exposing the adhesive, and press the base portions 68 against a patient to adhere the securement apparatus 60 containing the medical article 66 to the patient's skin.

As shown in FIGS. 10-13, in another embodiment, a securement device 80 includes a cover 82 or lid for covering and gripping the securement body 62. The cover 82 is preferably attached to one of the base portions 68 via a hinge, pivot joint, or similar structure. The hinge may take various forms. For example, a hinge may include a tongue 84 on the cover 82 and a groove 86 formed in a hinge element 72 on the base portion 68. A hinge may alternatively include a conventional pin-hinge mechanism, a snap-fitting mechanism including a snap-arm and a snap-receptacle, or any other suitable hinge or pivot joint.

Figure 12:
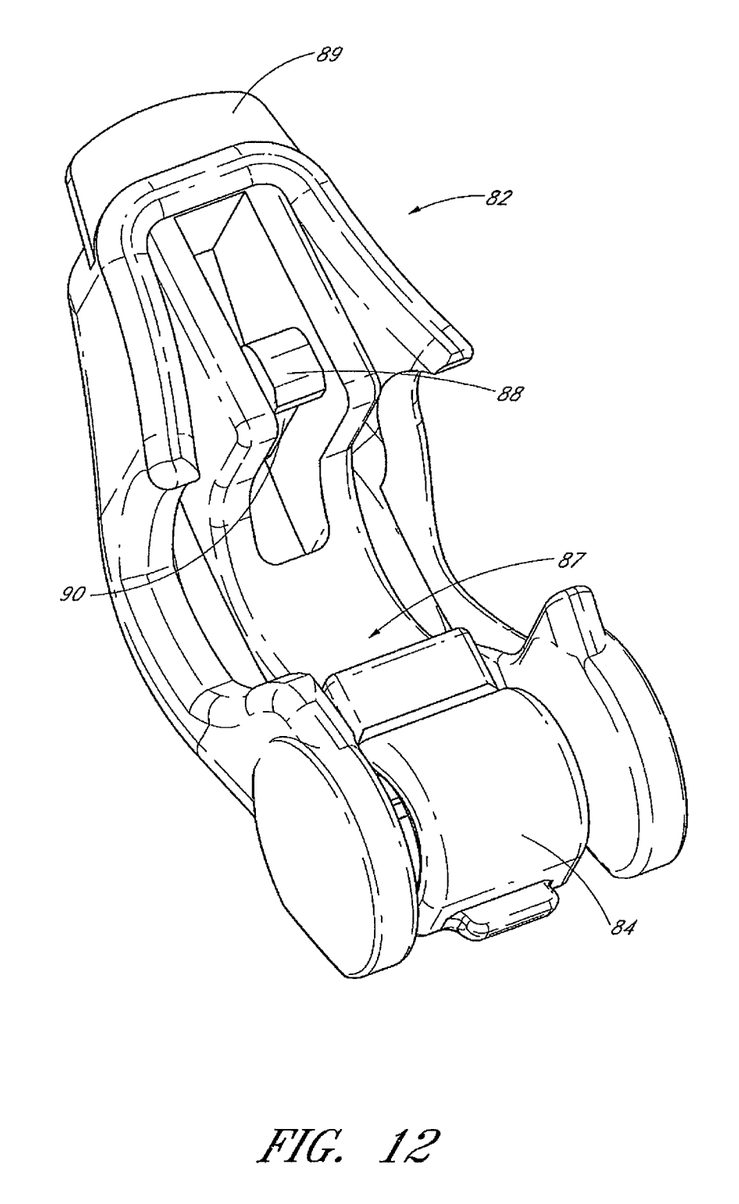
FIG. 12 is a bottom perspective view of the cover of the securement device shown in FIG. 10.
Figure 13:
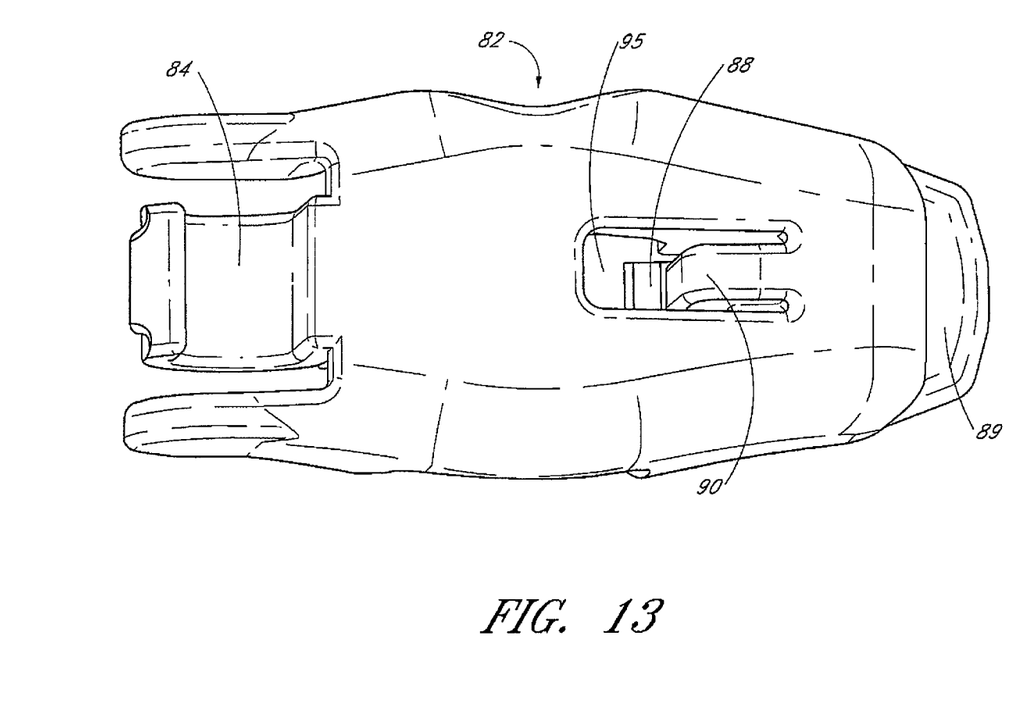
FIG. 13 is a top perspective view of the cover of the securement device shown in FIG. 10.

The cover 82 preferably includes a receiving region 87 configured to grip or squeeze the securement body 62, and a lever 89 or handle for allowing an attendant to manipulate the cover 82. The cover 82 further includes a latch element 88 for engaging the latch receptacle 70 in the securement body 62. The latch element 88 is preferably supported on a release arm 90, which is accessible via an opening 95 in the cover 82. The release arm 90 is pressable toward the lever end of the cover 82 for releasing the latch element 88 from the latch receptacle 70, which allows the cover 82 to be pivoted into the open position.

Any other suitable latch mechanism may alternatively be included. For example, the lever end of the cover 82 may include a latch element for engaging a latch receptacle supported on the base portion 68 opposite the one supporting the hinge element 72. Alternatively, a latch element may be positioned on the base portion 68 and a latch receptacle may be included in the cover 82. In another alternative embodiment, the hinge may be omitted and the cover 82 or lid may snap over the securement body 62 into receiving elements on both base portions 68 via latch or lock elements at both ends of the cover 82.

Figure 10:
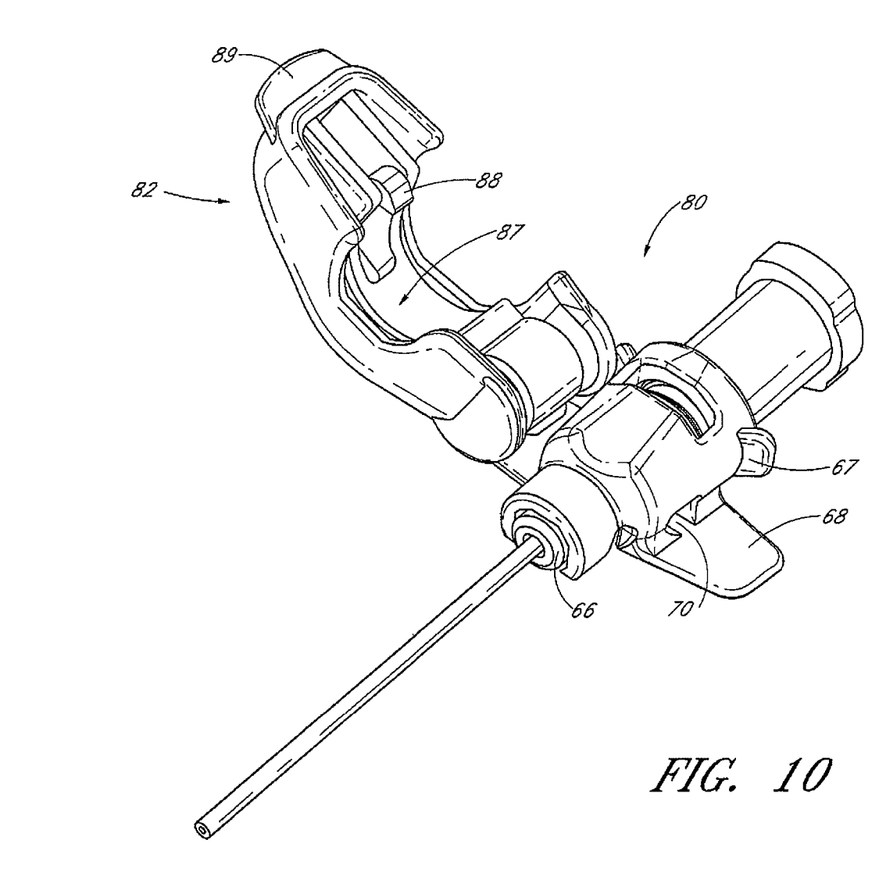
FIG. 10 is a perspective view of a securement device, according to another embodiment.
Figure 11:
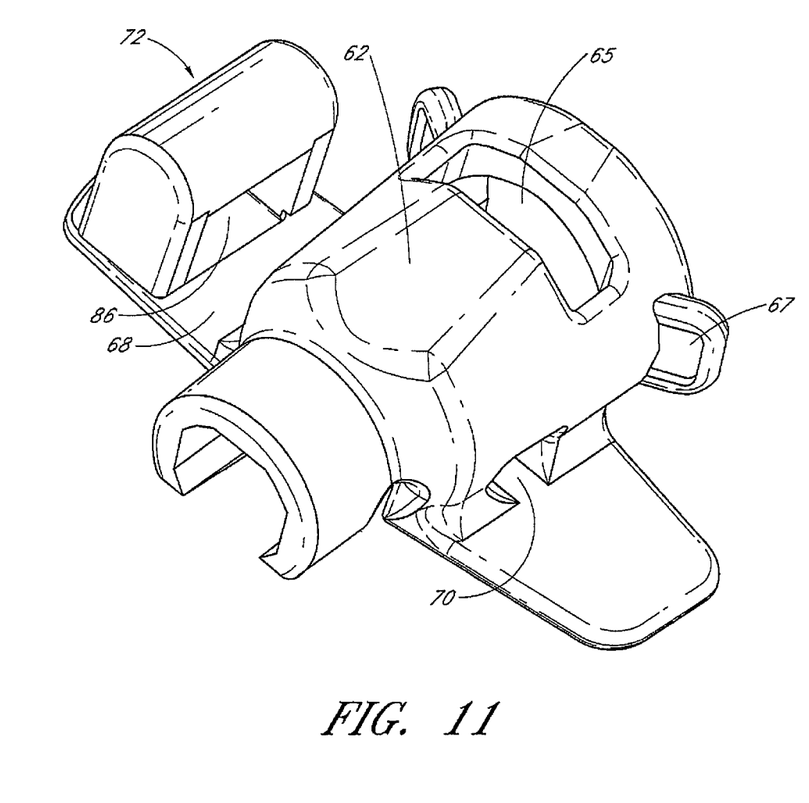
FIG. 11 is a perspective view of the securement body and hinge element of the securement device shown in FIG. 10.

In use, an attendant may pull the base portions 68 laterally away from each other to widen the central opening in the securement body 62 so that it may be placed over a medical article 66. The attendant may then release the base portions 68 so that the securement body 62 closes or conforms around the medical article 66, as shown in FIG. 10. Because the gripping cover 82 is included, the securement body 62 does not necessarily have to securely grip the medical article 66 without the aid of the cover 82, but it may optionally do so. The attendant may then pivot the cover 82 to the closed position, in which the latch element 88 engages the latch receptacle 70. In this closed position, the walls of the receiving region 87 grip or squeeze the outer walls of the securement body 62 toward the medical article 66 such that the engagement members 67 securely grip or squeeze the medical article 66. The attendant may then remove the peelable strips, exposing the adhesive, and press the base portions 68 against a patient to adhere the securement device 80 containing the medical article 66 to the patient's skin.

It is to be understood that not necessarily all objects or advantages disclosed herein may be achieved in accordance with any particular embodiment. Thus, for example, those skilled in the art will recognize that embodiments may be carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct a device and/or system in accordance with principles of this invention.

While the illustrative embodiments have been described with particularity, it will be understood that various other modifications will be apparent to and can be readily made by those skilled in the art without departing from the spirit and scope of the invention. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but by a fair reading of the claims that follow.

What is claimed is:

1. A retainer for a medical article comprising:
    a body member forming a channel configured to receive at least a portion of the medical article, the channel having a longitudinal axis, the body member being biased toward a closed position and movable to an open position, the portion of the medical article being secured in the channel at least when the body member is in the closed position;
    at least one or more actuators coupled to the body member and configured to expand the channel and move the body member to the open position so as to receive the portion of the medical article in the channel;
    a base portion at least partially surrounding a portion of the body member on opposite sides of the longitudinal axis, the base portion having one or more passageways configured to receive at least a portion of the one or more actuators.

2. The retainer of claim 1, further comprising a plurality of engagement members extending from an inner surface of the body member towards the longitudinal axis so as to contact the secured portion of the medical article at least when the body member is in the closed position.

3. The retainer of claim 2, wherein the plurality of engagement members extend from the inner surface of the body member at angles of between 25 and 65 degrees.

4. The retainer of claim 2, wherein the plurality of engagement members extend from the inner surface of the body member in a distal direction.

5. The retainer of claim 2, wherein at least one of the plurality of engagement members extends in a first direction and another one of the plurality of engagement members extends in a second direction, the second direction being different than the first direction.

6. The retainer of claim 1, wherein the body member comprises at least one opening, the opening being configured to receive an outwardly extending member of the medical article.

7. The retainer of claim 1, wherein at least a portion of the channel is tapered in the longitudinal direction.

8. The retainer of claim 1, further comprising a pad supporting the base portion and having a lower surface, at least a portion of the lower surface being covered by an adhesive for securing the retainer to the body of a patient.

9. The retainer of claim 1, wherein the longitudinal axis of the channel is at an angle of between 0 and 20 degrees with respect to a lower surface of the base portion.

10. The retainer of claim 1, wherein the body member comprises one or more abutment surfaces on a distal end of the base portion, the abutment surfaces configured to contact the medical article and to inhibit longitudinal movement of the medical article relative to the retainer.

11. The retainer of claim 1, wherein the at least one or more actuators are coupled to the body member at a location below the longitudinal axis of the channel.

12. The retainer of claim 11, wherein there are two actuators, the actuators coupled to the body member on opposite sides of the channel and movement of the actuators towards one another manipulates the body member to the open position.

13. The retainer of claim 1, further comprising one or more inner walls protruding inwardly toward the longitudinal axis of the channel, the one or more inner walls configured to prevent the medical article from moving longitudinally within the channel.

14. The retainer of claim 1, wherein the body member comprises an opening exposing a bottom of the channel so as to allow at least ingress of the medical article into the channel.

15. A retainer for a medical article comprising:
a body member forming a channel configured to receive at least a portion of a medical article, the channel having a longitudinal axis, the body member being made of a first material and being biased toward a closed position and movable to an open position, the portion of the medical article being secured in the channel at least when the body member is in the closed position;
a separate base portion at least partially surrounding a portion of the body member on opposite sides of the longitudinal axis, the base portion being made of a second material;
at least one or more actuators coupled to the body member and being configured to expand the channel and move the body member to the open position so as to receive the portion of the medical article in the channel, at least a portion of the at least one or more actuators being made from a third material, the third material being different from at least one of the first material and second material; and
a pad supporting the base portion and having a lower surface, at least a portion of the lower surface being covered by an adhesive.

16. The retainer of claim 15, wherein the third material is metal.

17. The retainer of claim 15, wherein the third material is plastic.

* * * * *